United States Patent [19]

Ohsaka et al.

[11] Patent Number: 4,864,040

[45] Date of Patent: Sep. 5, 1989

[54] MONOHALOGENOTRIFLUOROOXETANE AND ITS PREPARATION

[76] Inventors: Yohnosuke Ohsaka, 16-5, Shirakawa 1-chome, Ibaraki-shi, Osaka-fu; Satoru Kohno, Urbanland Aikawa No. 403, 1-1-43, Itakano, Higashi Yodogawa-ku, Osaka-shi, Osaka-fu, both of Japan

[21] Appl. No.: 73,590

[22] Filed: Jul. 14, 1987

[30] Foreign Application Priority Data

Jul. 14, 1986 [JP] Japan .................. 61-166426

[51] Int. Cl.$^4$ ........................................... C07D 305/04
[52] U.S. Cl. .................................................... 549/511
[58] Field of Search ................................ 549/510, 511

[56] References Cited

FOREIGN PATENT DOCUMENTS

| 0136668 | 4/1985 | European Pat. Off. |
| 0148482 | 7/1985 | European Pat. Off. |
| 0148490 | 7/1985 | European Pat. Off. |
| 0179443 | 4/1986 | European Pat. Off. |
| 0182132 | 5/1986 | European Pat. Off. |

OTHER PUBLICATIONS

Weinmayer, J. Org. Chem. 28 pp. 492–494 (1963).

*Primary Examiner*—Richard L. Raymond
*Assistant Examiner*—Mark W. Russell

[57] ABSTRACT

A novel monohalogenotrifluorooxetane of the formula:

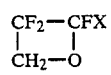

(I)

or

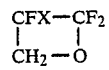 (II)

(wherein X is chlorine, bromine or iodine)

which is prepared by reacting monohalogenotrifluoroethylene of the formula:

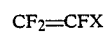

(III)

(wherein X is the same as defined above)

with a compound having a —(CH$_2$O)— unit.

7 Claims, No Drawings

MONOHALOGENOTRIFLUOROOXETANE AND ITS PREPARATION

BACKGROUND OF THE INVENTION

1. Field of the Invention

The present invention relates to a novel monohalogenotrifluorooxetane and a method for preparing the same.

2. Description of the Prior Arts 2,2,3,3-Tetrafluorooxetane is a known compound and can be prepared by reacting tetrafluoroethylene and paraform in anhydrous hydrogen fluoride (cf. J. Org. Chem., 28, 492-494(1963)). 2,2,3,3-Tetrafluorooxetane is polymerized to prepare a fluorine-containing polyether (cf. European Patent Publication No. 0148482 A2 and U.S. patent application Ser. No. 684,345 now abandoned). 2,2,3,3-Tetrafluorooxetane and a diamine are reacted to prepare a fluorine-containing polyaminoamide (cf. European Patent Publication No. 01821232 A2 and U.S. patent application Ser. No. 786,682 now U.S. Pat. No. 4,683,289). 2,2,3,3-Tetrafluorooxetane and a monoamine are reacted to prepare an amine amide (cf. European Patent Publication No. 0179443 A2 and U.S. patent application Ser. No. 786,681 now abandoned).

SUMMARY OF THE INVENTION

The present invention provides a novel monohalogenotrifluorooxetane of the formula:

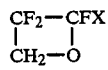  (I)

or

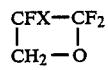  (II)

wherein X is chlorine, bromine or iodine.

The present invention also provides a method for preparing monohalogenotrifluorooxetanes (I) or (II) which comprises reacting a monohalogenotrifluoroethylene of the formula:

$$CF_2=CFX \quad (III)$$

(wherein X is the same as defined above) with a compound having a —(CH$_2$O)— unit.

DETAILED DESCRIPTION OF THE INVENTION

Examples of oxetane (I) or (II) according to the present invention are as follows:

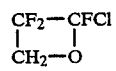  (1)

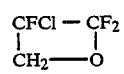  (2)

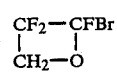  (3)

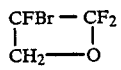  (4)

  (5)

  (6)

The oxetane (I) or (II) according to the present invention can be prepared by reacting a monohalogenotrifluoroethylene (III) with a compound having a —(CH$_2$O)— unit and can easily be decomposed to the unit (e.g. paraformaldehyde or trioxane). The reaction is preferably carried out in the presence of hydrogen fluoride.

A molar ratio of a monohalogenotrifluoroethylene (III) to the —(CH$_2$O)— unit is 0.5:1 to 10:1, preferably about 1:1. Hydrogen fluoride, which is preferably present, is used in an amount of 3 to 20, more preferably 5 to 10 moles per mole of the —(CH$_2$O)— unit. Usually a reaction temperature is from 20° to 100° C., preferably from 40° to 50° C. The reaction is carried out in a liquid phase. Reaction time varies with other reaction conditions such as the reaction temperature and is usually from 10 to 20 hours. Oxetane (I) or (II) is separated from a reaction mixture by a conventional method such as distillation.

Oxetane (I) or (II) is ring-opening polymerized to produce a linear polymer having substantially no side chain. In addition, oxetane (I) or (II) is more reactive than 2,2,3,3-tetrafluorooxetane and can be reacted with another compound to produce a compound having useful properties.

For example, oxetane (I) or (II) is reacted with thiourea to produce a mixture of compounds of the formulae:

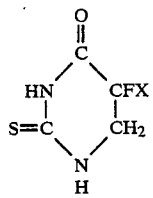  (IV)

and

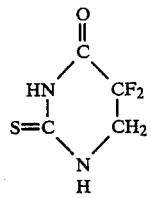  (V)

wherein X is the same as defined above. In the reaction, a molar ratio of oxetane (I) or (II) to thiourea is preferably 1:1 to 1:5, more preferably 1:3. A reaction temperature is from 0° to 50° C., preferably from 0° to 10° C. Reaction time varies with other conditions such as the reaction temperature and is usually 1 to 2 hours. An ether, such as ethylene glycol dimethyl ether is preferably used as a solvent.

Compound (V) may be used as a microbicide.

Compound (IV) is dehydrohalogenated to produce 5-fluorothiouracil. The dehydrohalogenation is usually carried out after isolating compound (IV) from the reaction mixture of oxetane (I) or (II) and thiourea, but the reaction mixture itself may be dehydrohalogenated. The dehydrohalogenation can be carried out by using, for example, a base such as sodium alkoxide. A molar ratio of compound (IV) to sodium alkoxide is preferably 1:1 to 1:2, more preferably 1:1. A reaction temperature is from 0° to 50° C., preferably 0° to 25° C. Reaction time varies with other conditions such as the reaction temperature and is varied from 1 to 24 hours. An alcohol such methanol can be used as a solvent.

According to Chemical Abstracts 61, 5664h, 5-fluorothiouracil and Raney nickel are refluxed in 2% aqueous ammonia solution for 2 to 4 hours to produce 5-fluorouracil having an anti-tumor activity.

The present invention will be hereinafter explained further in detail by the following examples.

EXAMPLE 1

In a 300 ml SUS-316 autoclave equipped with a stirrer, paraformaldehyde (20 g, 0.66 mol) was charged. A pressure in the autoclave was decreased and hydrogen fluoride (produced by Daikin Industries Ltd.) (140 g) was added. Chlorotrifluoroethylene ($CF_2=CFCl$) was injected from a valve of the autoclave through a copper tube of 2/8 inch in diameter to pressurize the autoclave interior to 4.5 kg/cm²G (at room temperature). Then the autoclave was heated to 45°–54° C. with stirring in an oil bath, the reaction was continued for 13 hours with injecting chlorotrifluoroethylene to maintain said pressure. The reaction mixture was poured into ice water. A lower organic layer was separated and distilled under reduced pressure to give a mixture of 3-chloro-2,2,3-trifluorooxetane and 2-chloro-2,3,3-trifluorooxetane (8.4 g). Boiling temperature: 22°–24° C. (120 mm/Hg).

Gas chromatography analysis (DC 550 column of 3 m in length, heated from 50° C. to 200° C. at a rate of 10° C./min) revealed that the mixture contained 46% by weight of 3-chloro-2,2,3-trifluorooxetane and 36% by weight of 2-chloro-2,3,3-trifluorooxetane.

Mass spectrometry

3-Chloro-2,2,3-trifluorooxetane: m/z=146 (M+), 127 (M-19(F)), 116 (M-30($CH_2O$)), 111 (M-35($Cl^-$)), 80 ($CFClCH_2^+$).

2-Chloro-2,3,3-trifluorooxetane: m/z=146 (M+), 127 (M-19(F)), 116 (M-30($CH_2O$)), 111 (M-35($Cl^-$)), 64 ($CF_2CH_2^+$).

EXAMPLE 2

In the same manner as in Example 1 but using bromotrifluoroethylene in place of chlorotrifluoroethylene, a reaction was carried out to produce a mixture of 72% by weight of 3-bromo-2,2,3-trifluorooxetane and 28% by weight of 2-bromo-2,3,3-trifluorooxetane. Boiling point: 44°–46° C. (120 mmHg).

Mass spectrometry

3-Bromo-2,2,3-trifluorooxetane: m/z=190 (M+), 172 (M-19(F)), 161 (M-30($CH_2O$)), 112 (M-79($Br^-$)), 124 ($CFBr-CH_2^+$).

2-Bromo-2,3,3-trifluorooxetane: m/z=190 (M+), 172 (M-19(F)), 161 (M-30($CH_2O$)), 112 (M-79($Br^-$)), 64 ($CF_2-CH_2^+$).

EXAMPLE 3

In a 50 ml eggplant type flask, ethylene glycol dimethyl ether (20 ml) and thiourea (3.4 g, 45 mmol) were charged and stirred. A mixture of 3-chloro-2,2,3-trifluorooxetane and 2-chloro-2,3,3-trifluorooxetane (2.2 g) (purity by gas chromatography: 46% by weight of 3-chloro-isomer and 36% by weight of 2-chloro-isomer) was dropwise added. After the completion of the addition, the reaction was continued at room temperature for 15 hours. Precipitates were recovered to give a white solid product (1.2 g). ¹H-NMR and ¹⁹F-NMR revealed that the product was a mixture of the following compounds:

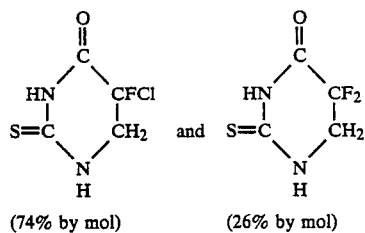

(74% by mol)   (26% by mol)

¹H-NMR (DMSO-d₆): δ(ppm)=3.8(—$CF_2$—C$\underline{H}$₂—NH—, t), 3.8–4.1(—CFCl—C$\underline{H}$₂—NH—), 8.8(—CO—NH—CS—NH—, br.).

¹⁹F-NMR (DMSO-d₆): δ(ppm)=30.1(—CO—$CF_2$—$CH_2$—, t), 36.1(—CO—CFCl—$CH_2$, t).

In a 50 ml eggplant type flask, methanol (20 ml) and the above produced crude product (0.85 g, 4.7 mmol) were charged. A 28% by weight solution of sodium methoxide in 20 ml of methanol (sodium methoxide 4.7 mmol) (available from Wako Pure Chemical Industries Ltd.) was dropwise and slowly added with stirring at room temperature over 30 minutes. After completion of the addition, the reaction was continued for 15 hours. Precipitates were filtrated off and methanol was evaporated off from a filtrate to give a white solid (0.5 g). The solid was washed with ethylene glycol dimethyl ether (20 ml) to give a product (0.4 g). Mass spectrometry, ¹H-NMR and ¹⁹F-NMR revealed that the product was a mixture of the following compounds:

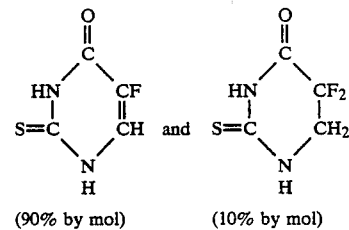

(90% by mol)   (10% by mol)

Total yield of 5-fluorothiouracil: 50%.

What is claimed is:

1. Monohalogenotrifluorooxetane of the formula:

or

wherein X is chlorine, bromine or iodine.
2. Monohalogenotrifluorooxetane according to claim 1, which is 3-Chloro-2,2,3-trifluorooxetane.
3. Monohalogenotrifluorooxetane according to claim 1, which is 2-Chloro-2,3,3-trifluorooxetane.
4. Monohalogenotrifluorooxetane according to claim 1, which is 3-Bromo-2,2,3-trifluorooxetane.
5. Monohalogenotrifluorooxetane according to claim 1, which is 2-Bromo-2,3,3-trifluorooxetane.
6. Monohalogenotrifluorooxetane according to claim 1, which is 3-Iodo-2,2,3-trifluorooxetane.
7. Monohalogenotrifluorooxetane according to claim 1, which is 2-Iodo-2,3,3-trifluorooxetane.

* * * * *

UNITED STATES PATENT AND TRADEMARK OFFICE
CERTIFICATE OF CORRECTION

PATENT NO. : 4,864,040

DATED : September 5, 1989

INVENTOR(S) : Yohnosuke OHSAKA et al

It is certified that error appears in the above-identified patent and that said Letters Patent is hereby corrected as shown below:

Please amend the front page of the patent to reflect the following Assignee information:

--[73] Assignee: Daikin Industries Ltd.
Osaka-fu, Japan --

Signed and Sealed this

Twenty-first Day of August, 1990

Attest:

HARRY F. MANBECK, JR.

*Attesting Officer*  *Commissioner of Patents and Trademarks*